(12) United States Patent
Kan et al.

(10) Patent No.: US 9,896,399 B2
(45) Date of Patent: Feb. 20, 2018

(54) SELECTIVE HYDROGENATION METHOD FOR PHENYLACETYLENE IN THE PRESENCE OF CRACKING C8 FRACTION

(71) Applicant: Guangdong Xinhuayue Huade Technology Co., Ltd., Guangdong (CN)

(72) Inventors: Yiqun Kan, Maoming (CN); Hajian Pang, Maoming (CN)

(73) Assignee: Guangdong Xinhuayue Huade Technology Co., Ltd., Maoming, Guangdong (CN)

( * ) Notice: Subject to any disclaimer, the term of this patent is extended or adjusted under 35 U.S.C. 154(b) by 447 days.

(21) Appl. No.: 14/051,493

(22) Filed: Oct. 11, 2013

(65) Prior Publication Data

US 2014/0114102 A1   Apr. 24, 2014

(30) Foreign Application Priority Data

Oct. 18, 2012   (CN) .......................... 2012 1 0396358

(51) Int. Cl.
   C07C 7/167   (2006.01)
   C07C 7/163   (2006.01)

(52) U.S. Cl.
   CPC .................................. C07C 7/167 (2013.01)

(58) Field of Classification Search
   CPC .................................. C07C 7/167; C07C 15/46
   See application file for complete search history.

(56) References Cited

U.S. PATENT DOCUMENTS 3,644,197 A * 2/1972 Kelley ................... C10G 65/12
                                                      208/254 H
4,658,080 A * 4/1987 McFarland ............ B01J 23/755
                                                      585/260
5,368,824 A * 11/1994 Nell ........................ F23C 10/20
                                                      110/245

(Continued)

FOREIGN PATENT DOCUMENTS

CN          1852877 A       10/2006
CN          101475438 A      7/2009
CN          102408299 A *    4/2012

OTHER PUBLICATIONS

CN 102408299A translation.*

Primary Examiner — Brian A McCaig
Assistant Examiner — Jason Y Chong
(74) Attorney, Agent, or Firm — Innovation Capital Law Group, LLP; Vic Lin

(57) ABSTRACT

Provided is a method for selective hydrogenation phenylacetylene (PA) in cracked C8 fraction, which adopts a hydrogenation reactor featuring an upper catalyst bed and a lower catalyst bed, and operated by the following steps: feedstock cracked C8 fraction is supplied through the lower bed while hydrogen is supplied through the gas distributor located below the lower bed and increases the bed temperature to 0-20° C., and gas distributor located below the upper bed increases the upper bed temperature to 0-15° C., the reaction effluent from the upper bed is subsequently passed through and recovered from the packing layer. The method is characterized with low loss rate of styrene after hydrogenation and high hydrogenation rate of phenylacetylene.

20 Claims, 2 Drawing Sheets

(56) References Cited

U.S. PATENT DOCUMENTS

| | | | | |
|---|---|---|---|---|
| 6,555,073 B1* | 4/2003 | Butler | ............... | C07C 5/09 422/171 |
| 6,747,181 B1* | 6/2004 | Bosman | ............... | C07C 7/167 585/258 |
| 2005/0027149 A1* | 2/2005 | Merrill | ............... | C07C 5/09 585/266 |
| 2010/0174099 A1* | 7/2010 | Behkish | ............... | B01J 8/006 549/518 |
| 2011/0308999 A1* | 12/2011 | Li | ............... | B01J 23/44 208/141 |
| 2013/0165711 A1* | 6/2013 | Dandeu | ............... | C07C 5/03 585/251 |

* cited by examiner

SELECTIVE HYDROGENATION METHOD FOR PHENYLACETYLENE IN THE PRESENCE OF CRACKING C8 FRACTION

PRIORITY

This application claims priority to a Chinese Patent Application filed on Oct. 18, 2012, and assigned Serial No. 201210396358.1, the content of which is incorporated herein by reference.

BACKGROUND

1. Field of Technology

This invention relates to a process for removing phenylacetylene contaminants from styrene, particularly relating to a selective hydrogenation method for phenylacetylene in the presence of C8 fraction, a byproduct in the process of ethylene cracking from petroleum hydrocarbon. This technical proposal can hydrogenate phenylacetylene in the fractions, whereas the content of styrene remains un-hydrogenated or is enhanced; hydrogenated C8 fraction produces minor amount of gum, and can be used as feedstock for petroleum hydrocarbon cracking C8 fraction in the process of styrene extraction.

2. Background

Ethylene cracked gasoline contains high level of aromatics, which is rich in styrene. A set of 1000 kt ethylene cracking apparatus can crack nearly 5% of styrene from gasoline and 40% of those from C8 fraction which is rich in styrene. In the prior art, C6-C8 fractions are directly undergone two-stage hydrogenation, hydrogenating and extracting unsaturated aromatics such as styrene. Eventually, styrene is recovered in the form of ethylbenzene in the presence of dimethylbenzene. Dimethylbenzene normally contains 40-60% of ethylbenzene, which will affect its yields if used directly as PX feedstock so as to impact cost-effectiveness. It will bring significant benefits if styrene can be extracted from C8 fraction. In recent years, the production of cracked gasoline is growing along with the increase of million ton of ethylene cracking plants establishing in China. Breakthrough technology for extracting and recycling styrene from cracked gasoline and its application in industry become the key and the focus point.

C8 fraction contains high level of styrene and minor amount of phenylacetylene. Phenylacetylene and styrene share similar chemical structure, therefore they have similar choices of extraction solvents. If styrene is extracted directly, phenylacetylene will be extracted along side. C8 fraction from ethylene cracked gasoline contains nearly 0.1~1% of phenylacetylene. The purity and quality of styrene products are difficult to improve because of the presence of phenylacetylene. Therefore, phenylacetylene must be removed before styrene is extracted in order to obtain polymer-grade styrene products.

Presently, the best way to remove phenylacetylene from cracked gasoline is to selectively hydrogenate phenylacetylene and convert it into ethylbenzene or styrene.

Chinese patent CN1852877A discloses a method that involves reducing phenylacetylene contaminants in the presence of styrene monomers. A styrene monomer stream containing minor amount of phenylacetylene and a hydrogenation gas containing hydrogen are supplied to the hydrogenation reactor. The styrene monomer stream and the hydrogen are brought into contact with a catalyst bed containing a hydrogenation catalyst comprising a reduced copper compound on theta θ-alumina support. The hydrogenation reactor is operated at a temperature of at least 60° C. and a pressure of at least 30 psig to hydrogenate phenylacetylene to produce styrene. This technique features high reaction temperature, incomplete hydrogenation of phenylacetylene (70%), and high loss rate of styrene (nearly 3% styrene is converted into ethylbenzene).

Chinese patent CN101475438A discloses another selective hydrogenation method for phenylacetylene in the presence of styrene, mainly aiming to solve the problem of high loss rate of styrene in prior art. Said invention uses hydrocarbon fraction containing phenylacetylene as feedstock; reaction temperature is within the range of 15~100° C.; weight space velocity is within the range of 0.01~100 $h^{-1}$; a molar ratio of hydrogen to phenylacetylene in the range of 1~30:1; reaction pressure is within the range of −0.08~5.0 Mpa. Under the condition, feedstock is brought to contact with a catalyst containing carbon oxide. Phenylacetylene in the reaction effluent is then hydrogenated to styrene. Said technique solves the problem of high loss rate of styrene. However, the hydrogenation of phenylacetylene is incomplete and generates gum after hydrogenating. Gum formation in feedstock leads to loss of styrene and consequently the polymers are left in the solvent during following process of styrene extraction and distillation, resulting in low extraction rate of solvent. In addition, the remained gum left at the surface of catalyst will gradually lower the catalyst performance and further deactivate catalyst, eventually shorten the catalyst lifetime.

SUMMARY

A first aspect provides a selective hydrogenation method for phenylacetylene in cracked C8 fraction. Said method permits to hydrogenate phenylacetylene in styrene, whereas styrene is not hydrogenated into ethylbenzene, and hydrogenated fraction only contains minor amount of gum. Hydrogenated styrene contains less than 15 ppm phenylacetylene. The content of styrene has minimal loss or is enhanced.

A second aspect provides a selective hydrogenation method for phenylacetylene in the cracked C8 fraction. It can be carried out with a hydrogenation reactor featuring an upper catalyst bed and a lower catalyst bed. This invention is carried out as below:

a) crude cracked C8 fraction is supplied through the bottom of the lower bed while hydrogen is supplied from the gas distributor located below the lower bed and bed temperature is increased to a temperature within the range of 0~20;

b) hydrogen is supplied through the gas distributor located below the upper bed and raises the upper bed temperature to a temperature within the range of 0~15° C., reaction effluent coming out from the upper bed subsequently being recovered after flowing through packing layer;

wherein the hydrogenation reactor is operated in accordance with following conditions: reactor inlet temperature is in the range of 5~40° C.; reaction pressure is in the range of 0.1~4.0 MPag; hydrogen oil ratio of lower bed is in the range of 0.1~50; reaction oil space velocity is in the range of 0.1~35 $h^{-1}$.

The selective hydrogenation reaction of phenylacetylene in the presence of styrene of this invention is a three-phrase reaction including gas, liquid and solid phases. When space velocity is low, it tends to form a rill flow when using regular trickle-bed reactor. Therefore it will cause hot spots in the reactor, in severe condition, resulting in explosive polymerization of styrene and catalyst deactivation.

In this invention, gas and liquid feeds are supplied from the lower end of the reactor. An adiabatic fixed-bed reactor with concurrent flows is employed. The upper bed and the lower bed are loaded with catalysts correspondingly. Gas and feedstock are supplied to the reactor in two stages, ensuring the uniformity of hydrogen and C8 fraction (mainly phenylacetylene) ratio at each cross section of the hydrogenation reactor bed. This method provides an advanced solution to minimize maldistribution of gas-liquid phases in hydrogenation reactor, preventing formation of hot spots and the explosive polymerization of styrene.

Catalysts are required to pack homogenously in the upper bed and lower bed in order to prevent feedstock forming a rill flow. The combined packing volume of the catalysts in the upper bed and lower bed counts for 70~80% of the total volume of the hydrogenation reactor, and the weight ratio of the catalysts in the upper bed to those in the lower bed is 1:1~0.5; preferably, the weight ratio of the catalysts in the upper bed to those in the lower bed is within the range of 1:0.8~0.6.

Gas is supplied in two stages. Gas (hydrogen) supplied from the bottom of the reactor and liquid feed (crude cracked C8 fraction) react with the catalyst at the lower bed, releasing heat to increase the bed temperature rapidly. By regulating the cold air in the intermediate zone between the upper bed and the lower bed (that is the hydrogen supplied from gas distributor located below the upper catalyst bed), the amount of the feed stream is able to control the increase of the upper bed temperature, thus effectively regulating bed temperature and preventing the hydrogenation of styrene.

In this invention, the requirement of crude cracked C8 fraction is not strict. For instance, phenylacetylene in crude cracked C8 fraction is present in an amount of 0.01~2 wt %, and C9+ is ≤0~5 wt %, and styrene is present in an amount of 15~70 wt %.

Commonly used catalysts are able to meet the fundamental requirement of this invention, bring acceptable results and achieve the objective of the invention. However, in order to achieve complete hydrogenation of phenylacetylene, lower styrene loss and prevent catalyst failure to extend its lifetime, the following catalyst is employed in this invention:

Said catalyst uses $Al_2O_3$—$SiO_2$, $Al_2O_3$ or $SiO_2$ as support, Ni as the active component, comprising at least one group IVB metal and at least one group VIB metal from the periodic table of elements and at least one alkali metal as additives;

Based on 100 wt % of catalyst, Ni is present within the range of 12~21 wt %; the group IVB metals are present in an amount of 0.6~8 wt %; the group VIB metals are present in an amount of 0.5~1.5 wt %; the alkali metal is 5~10 wt % of Ni;

Wherein the group IVB metals are Ti and Zr; the group VIB metals are Cr, Mo and W; the alkali metals are Li, Na and K.

Said catalyst has inadequate catalytic active centers if it has a low Ni content, which leads to incomplete hydrogenation of phenylacetylene; when said catalyst has high Ni content, it has excessive active centers which causes high loss rate of styrene. In general, Ni is present in an amount of 12~21 wt %, and preferably, within the range of 13~18 wt %. Desired amount of alkali metal is employed in the catalyst in order to regulate the acidity of the active centers, increasing the hydrogenation selectivity of the catalyst. In general, the alkali metal is present in an amount of 5~10 wt % of the Ni content, preferably within the range of 6~9 wt %.

In this invention, the supported catalyst has a BET specific surface area in the range of 140~200 $m^2/g$, a pore volume in the range of 0.2~0.5 ml/g, and an average pore diameter in the range of 10~25 nm, exhibiting parallel-peak structure. High specific surface area and suitable pore volume will improve the catalytic effectiveness of catalyst active component, and substantially reduce pressure drop in the catalyst bed.

Prepared catalyst is in oxidation state and doesn't process catalytic capability. It must be reduced to reduced state by high temperature hydrogen and regain catalytic capability prior to use.

Said catalyst can be prepared by routine loading method. For instant, $Al_2O_3$—$SiO_2$ support is first pre-impregnated in turn with group VIII metal salt solution, group IVB metal salt nitric acid solution and group VIB metal salt nitric acid solution, and subsequently impregnated in alkali metal or alkaline-earth metal compound water solution. The support is then dried at temperature 100~200° C. after each impregnation, and calcined for 2~10 hours at 400~700° C.

Said hydrogenation reactor has a circular cross section; gas distributor comprises an inner ring pipe and an outer ring pipe which are linked to a gas inlet vessel, connected by connection pipes and horizontally installed. Vent holes are evenly placed at the bottom of the inner ring pipe and the outer ring pipe. Ideally, both the inner and outer ring pipes have two loops of vent holes evenly spaced at the bottom. The inner-loop vent holes and outer-loop vent holes are located at either side of the ring pipe center and perpendicular to the center. Each hole center and the perpendicular line of the ring pipe center respectively form an angle within the range of 15~40 degree with respect to the perpendicular direction of the pipe center. Furthermore, each vent hole has a circular shape and the total surface dimensions of the holes is 1~3 times as the cross section of the ring pipe. This model enables homogeneous distribution of the gas and prevents catalyst powder from clogging the distributor tunnel.

Desired design combination of stock feeding system, reactor structure and gas distributor will effectively improve the efficiency of the gas-liquid-solid three-phase reaction. It also increases the conversion rate of phenylacetylene hydrogenation, effectively lower styrene loss and the formation of gum. Ideally, it permits remained phenylacetylene in C8 fraction being as low as 0, minimum styrene loss being 0, and the formation of gum equal to or less than 10 mg/ml.

Modest reaction condition such as low pressure, low temperature and low hydrogen consumption, helps reduce the polymerization of styrene and other unsaturated hydrocarbon as well as the formation of gum, prevent the accumulation of gum at the catalyst surface, prolong catalyst lifetime and ensure the operation of the device in a long period.

The catalyst is loaded to upper level and lower level, respectively. The gas is supplied from two stages. Gas and liquid stream distribute uniformly at low gas volume, preventing formation of hot spots and rill flows. Bed temperature is adjustable so that effectively prevents inlet stream from partially overheating and explosive polymerization of gum in the presence of high concentration of styrene.

Surface properties and acid properties of the catalyst for phenylacetylene selective hydrogenation permit selectively hydrogenation of phenylacetylene and reduce the tendency of unsaturated hydrocarbon polymerization of styrene and phenylacetylene. Such properties also enable styrene remain un-hydrogenated while the catalyst selectively hydrogenates phenylacetylene in the presence of high concentration of styrene. Said catalyst employed in this invention is characterized with low styrene loss after hydrogenation, and complete hydrogenation of phenylacetylene.

BRIEF DESCRIPTION

DETAILED DESCRIPTION

Having described specific hydrogenation reactor structure and catalyst employed in the following preferred embodiments, it will be understood that modification thereof may be suggested to those skilled in the art, and it is intended to cover all such modifications as fall within the scope of the claims.

Figure 1:
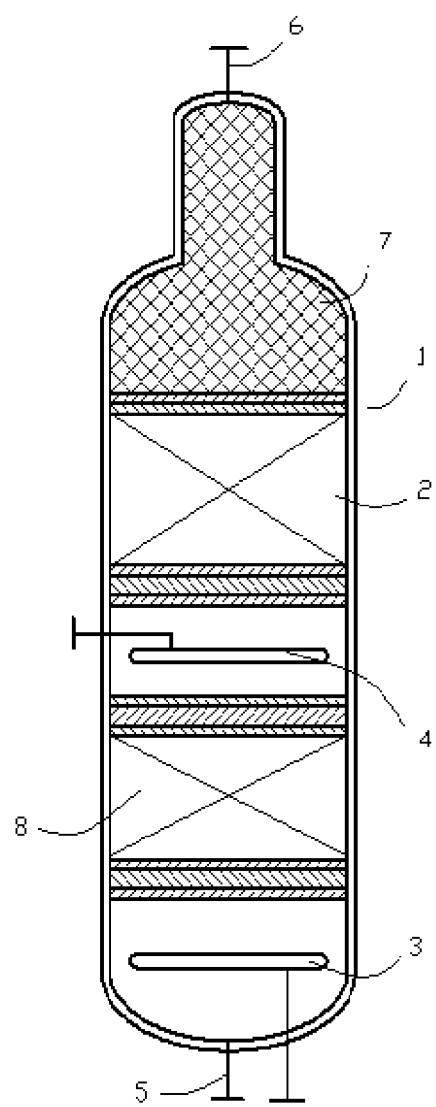
FIG. 1 illustrates the structural diagram of an embodiment of the hydrogenation reactor.
Figure 2:
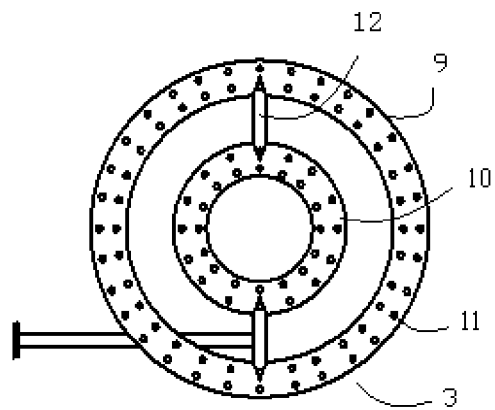
FIG. 2 illustrates the bottom view of an embodiment of the gas distributor in the hydrogenation reactor.
Figure 3:
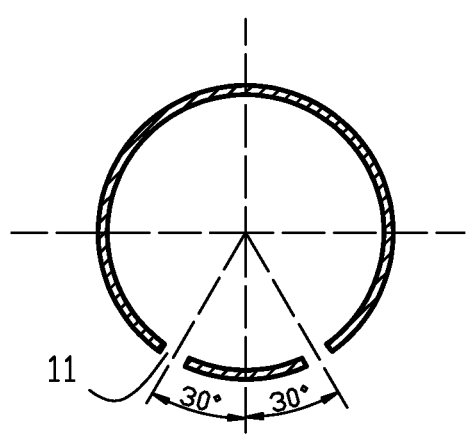
FIG. 3 illustrates the orientation diagram of an embodiment of the vent holes on the gas distributors.

Referring to FIG. 1, hydrogenation reactor adopts an adiabatic bubbling fixed-bed reactor with concurrent flows. Said reactor features an upper bed 2 and a lower bed 8. Inlet vessel 5 for crude cracked C8 fraction is located at the bottom of the reactor. Gas distributors 4 & 3 are placed under the upper bed 2 and the lower bed 8, respectively. The total packing volume of catalysts between the upper bed 2 and the lower bed 8 is 75 v % of the hydrogenation reactor 1. The weight ratio of the catalyst in the upper bed 2 to the lower bed 8 is 1:0.7. Hydrogenation reactor 1 has a circular cross section; gas distributor 3 comprises an inner ring pipe 10 and an outer ring pipe 9 which are horizontally installed, linked to a gas inlet vessel and connected by connection pipes 12. An inner loop and an outer loop of vent holes 11 are evenly positioned at the bottom of the inner ring pipe 10 and the outer ring pipe 9, respectively. Each vent hole has a circular shape and inner-loop vent holes and the outer-loop vent holes are placed at either side of perpendicular direction of the pipe center. Each hole center and the perpendicular line of the pipe center form a 30 degree angle with respect to the perpendicular direction of the pipe center. Referring to FIG. 2 and FIG. 3, the total dimensions of the vent holes is twice as the cross section of the ring pipe.

In this invention, the catalyst uses $Al_2O_3$—$SiO_2$ as support and is prepared by commonly known loading method. Based on 100 wt % of the catalyst, active component Ni is present in an amount of 16 wt %, additives including group IVB metal Zr present in an amount of 0.8 wt %, group VIB metal Cr present in an amount of 1.3 wt %; alkali metal K being 7 wt % of the Ni content. The supported catalyst has a BET specific surface area of 170 $m^2$/g, a pore volume of 0.35 ml/g, and a mean pore diameter of 17.5 nm.

Said catalyst is converted to reduced Ni-based catalyst by hydrogen activation at 400° C. for 4 hours in the hydrogenation reactor 1 prior to use, Embodiment 1

Feedstock cracked C8 is fed through cracked C8 inlet vessel 5 located under the lower bed 8 of the hydrogenation reactor 1. Hydrogen is supplied from the gas distributor 3 located under the lower bed 8 and increases lower bed temperature to 20° C. Next, hydrogen is introduced by the gas distributer 4 located under the upper bed 2 to increase the upper bed temperature to 0° C. Effluent from lower bed 8 continues to proceed to upper bed 2 followed by packing layer 7 and is subsequently recovered from discharging pipe 6. Said packing layer 7 uses packing material commonly used in hydrogenation reactions. Hydrogenation reactor 1 is operated at a reactor inlet temperature of 5° C., a reaction pressure of 4.0 MPag, hydrogen-oil ratio of the lower bed of 0.1, and a reaction oil-phase space velocity of 35 $h^{-1}$.

Ethylene cracked C8 fraction rich in dimethylbenzene is employed as feedstock, wherein styrene is present in an amount of 37.1 wt %, phenylacetylene is present in an amount of 0.64 wt %. Reaction results are shown in Table 1:

TABLE 1

| Compositions | C8 Fraction | Hydrogenated products after 10 hr reaction | Hydrogenated products after 30 hr reaction | Hydrogenated products after 45 hr reaction | Hydrogenated products after 80 hr reaction |
| --- | --- | --- | --- | --- | --- |
| methylbenzene | 0.25 | 0.25 | 0.25 | 0.25 | 0.25 |
| ethylbenzene | 9.43 | 10.01 | 9.58 | 9.58 | 9.49 |
| dimethybenzene | 48.51 | 47.5 | 47.89 | 48.66 | 48.66 |
| Styrene | 37.1 | 36.47 | 37.39 | 37.18 | 37.17 |
| phenylacetylene | 0.64 | 0.01 | 0 | 0 | 0 |
| C9+ fraction | 0.09 | 0.13 | 0.1 | 0.1 | 0.11 |
| gum | 12 mg/ml | 15 mg/ml | 14 mg/ml | 14 mg/ml | 12 mg/ml |

Embodiment 2

Operational procedure remains the same as Embodiment 1, whereas the controlling conditions of hydrogenation reactor 1 have been modified as bellowed: reactor inlet temperature is 40° C., reaction pressure is 0.1 MPag, the upper bed temperature is increased by 15° C., and the lower bed temperature is increased by 0° C., hydrogen-oil ratio of the lower bed is 50, reaction oil-phase space velocity is 0.1 $h^{-1}$.

Ethylene cracked C8 fraction rich in dimethylbenzene is employed as feedstock, wherein styrene is present in an amount of 37.1 wt %, phenylacetylene is present in an amount of 0.64 wt %. Reaction results are shown in Table 2:

TABLE 2

| Compositions | C8 Fraction | Hydrogenated products after 10 hr reaction | Hydrogenated products after 30 hr reaction | Hydrogenated products after 45 hr reaction | Hydrogenated products after 80 hr reaction |
| --- | --- | --- | --- | --- | --- |
| methylbenzene | 0.25 | 0.25 | 0.25 | 0.25 | 0.25 |
| ethylbenzene | 9.43 | 10.01 | 9.58 | 9.58 | 9.49 |
| dimethybenzene | 48.51 | 47.5 | 47.89 | 48.66 | 48.66 |
| Styrene | 37.1 | 36.47 | 37.39 | 37.18 | 37.17 |
| phenylacetylene | 0.64 | 0.01 | 0 | 0 | 0 |
| C9+ fraction | 0.09 | 0.13 | 0.1 | 0.1 | 0.11 |
| gum | 9 mg/ml | 12 mg/ml | 10 mg/ml | 15 mg/ml | 10 mg/ml |

Embodiment 3

Operational procedure remains the same as Embodiment 1, whereas the controlling conditions of hydrogenation 1 have been modified as bellowed: reactor inlet temperature is 50° C., reaction pressure is 0.5 MPag, the upper bed temperature is increased by 5° C., and the lower bed temperature is increased by 15° C., hydrogen-oil ratio of the lower bed is 40, reaction oil-phase space velocity is 15 $h^{-1}$.

Ethylene cracked C8 fraction rich in dimethylbenzene is employed as feedstock, wherein styrene is present in an amount of 37.1 wt %, phenylacetylene is present in an amount of 0.64 wt %. Reaction results are shown in Table 3:

TABLE 3

| Compositions | C8 Fraction | Hydrogenated products after 10 hr reaction | Hydrogenated products after 30 hr reaction | Hydrogenated products after 45 hr reaction | Hydrogenated products after 80 hr reaction |
| --- | --- | --- | --- | --- | --- |
| methylbenzene | 0.25 | 0.25 | 0.25 | 0.25 | 0.25 |
| ethylbenzene | 9.43 | 10.17 | 10.01 | 10.15 | 10.34 |
| dimethybenzene | 48.51 | 47.5 | 47.45 | 47.56 | 47.56 |
| Styrene | 37.1 | 36.37 | 36.39 | 36.25 | 36.22 |
| phenylacetylene | 0.64 | 0.01 | 0 | 0 | 0 |
| C9+ fraction | 0.09 | 0.15 | 0.16 | 0.16 | 0.18 |
| gum | 9 mg/ml | 13 mg/ml | 15 mg/ml | 15 mg/ml | 18 mg/ml |

Embodiment 4

Operation procedure remains the same as Embodiment 1, whereas the controlling conditions of hydrogenation 1 have been modified to: reactor inlet temperature being 20° C., reaction pressure being 1 MPag, the upper bed temperature being increased by 8° C., and the lower bed temperature being increased by 10° C., hydrogen-oil ratio of the lower bed being 20, reaction oil-phase space velocity being 5 $h^{-1}$.

Ethylene cracked C8 fraction rich in dimethylbenzene is employed as feedstock, wherein styrene is present in an amount of 37.1 wt %, phenylacetylene is present in an amount of 0.64 wt %. Reaction results are shown in Table 4:

TABLE 4

| Compositions | C8 Fraction | Hydrogenated products after 10 hr reaction | Hydrogenated products after 30 hr reaction | Hydrogenated products after 45 hr reaction | Hydrogenated products after 80 hr reaction |
| --- | --- | --- | --- | --- | --- |
| methylbenzene | 0.25 | 0.25 | 0.25 | 0.25 | 0.25 |
| ethylbenzene | 9.43 | 10.67 | 10.71 | 10.65 | 10.64 |
| dimethybenzene | 48.51 | 47.5 | 47.45 | 47.65 | 47.56 |
| Styrene | 37.1 | 36.57 | 36.59 | 36.45 | 36.62 |
| phenylacetylene | 0.64 | 0.01 | 0 | 0 | 0 |
| C9+ fraction | 0.09 | 0.15 | 0.16 | 0.16 | 0.13 |
| gum | 9 mg/ml | 13 mg/ml | 15 mg/ml | 15 mg/ml | 18 mg/ml |

Embodiment 5

Operation procedure remains the same as Embodiment 1, whereas the controlling conditions of hydrogenation 1 have being modified to: reactor inlet temperature being 35° C., reaction pressure being 0.6 MPag, the upper bed temperature being increased by 5° C., and the lower bed temperature being increased by 15° C., hydrogen-oil ratio of the lower bed being 40, reaction oil-phase space velocity being 35 $h^{-1}$.

Ethylene cracked C8 fraction rich in dimethylbenzene is employed as feedstock, wherein styrene is present in an amount of 37.1 wt %, phenylacetylene is present in an amount of 0.64 wt %. Reaction results are shown in Table 5:

TABLE 5

| Compositions | C8 Fraction | Hydrogenated products after 10 hr reaction | Hydrogenated products after 30 hr reaction | Hydrogenated products after 45 hr reaction | Hydrogenated products after 80 hr reaction |
|---|---|---|---|---|---|
| methylbenzene | 0.25 | 0.25 | 0.25 | 0.25 | 0.25 |
| ethylbenzene | 9.43 | 10.17 | 10.01 | 10.15 | 10.34 |
| dimethybenzene | 48.51 | 47.5 | 47.45 | 47.65 | 47.56 |
| Styrene | 37.1 | 36.37 | 36.39 | 36.25 | 36.22 |
| phenylacetylene | 0.64 | 0.01 | 0 | 0 | 0 |
| C9+ fraction | 0.09 | 0.15 | 0.16 | 0.16 | 0.18 |
| gum | 9 mg/ml | 13 mg/ml | 15 mg/ml | 15 mg/ml | 18 mg/ml |

What is claimed is:

1. A method for the selective hydrogenation of a cracked C8 fraction including styrene and phenylacetylene in a hydrogenation reactor loaded with a catalyst having an upper bed and a lower bed, the method comprising the steps of:
   a) feeding a feedstock comprising the cracked C8 fraction through a bottom of the lower bed at a first inlet temperature and contacting the feedstock with a first portion of the catalyst to produce a first hydrogenated product stream, wherein a temperature increase between the feedstock and the first hydrogenated product stream is controlled to be kept at 0-20° C. by introducing hydrogen from a first gas distributor positioned below the lower bed; and
   b) feeding the first hydrogenated product stream to the upper bed at a second inlet temperature and contacting the first hydrogenated product stream with a second portion of the catalyst to produce a second hydrogenated product stream, wherein a temperature increase between the first hydrogenated product stream and the second hydrogenated product stream is controlled to be kept at 0-15° C. by introducing hydrogen from a second gas distributer positioned below the upper bed; and
   c) sending the second hydrogenated product stream from the upper bed to a packing layer and recovering a hydrogenated product;
   wherein said hydrogenation reactor is operated at: a reactor inlet temperature in the range of 5-40° C., a reaction pressure in the range of 0.1-4.0 MPag, a hydrogen to feedstock ratio of the lower bed in the range of 0.1-50, a reaction oil phase space velocity within the range of 0.1-35 $h^{-1}$.

2. The method of claim 1, wherein phenylacetylene in the crude cracked C8 fraction is present in a range of 0.01-2 wt % and C9+ equals to or is less than 0-5 wt %, and styrene is present in the range of 15-70 wt %.

3. The method of claim 1, wherein a total packing volume of catalyst in the upper bed and the lower bed takes up 70-80 v % of the total volume of said hydrogenation reactor, a weight ratio of the catalyst loaded in the upper bed and the lower bed is in the range of 1:1-0.5.

4. The method of claim 3, wherein the weight ratio of the catalyst loading in the upper bed to those in the lower bed is in the range of 1:0.8-0.6.

5. The method of claim 1, wherein said catalyst comprises $Al_2O_3$—$SiO_2$, $Al_2O_3$ or $SiO_2$ as a support and Ni as an active component, and additives comprising at least one metal from the group IVB, at least one metal from group VIB and at least one alkali metal; further wherein a total mass content of catalyst being 100%, Ni is present within the range of 12-21 wt %; the group IVB metal is present within the range of 0.6-8 wt %; the group VIB metal is present in the range of 0.5-1.5 wt %; the alkali metal is present within the range of 5-10 wt %; the group IVB metals are Ti and Zr; the group VIB metals are Cr, Mo and W; Alkali metals are Li, Na, and K.

6. The method of claim 5, wherein Ni is present within the range of 6-9 wt %.

7. The method of claim 5, wherein a BET specific surface area of the support is within the range of 140-200 $m^2$/g, pore volume is within the range of 0.2-0.5 ml/g, mean pore diameter is within the range of 10-25 nm, exhibiting parallel-peak structure.

8. The method of claim 5, wherein said catalyst is activated by hydrogen at 400° C. for 4 hours in the hydrogenation reactor prior to use.

9. The method of claim 1, wherein the hydrogenation reactor has a circular cross section, the gas distributor comprises a horizontally installed inner ring pipe and an outer ring pipe, which are connected by connection pipes and linked to an air inlet vessel, wherein vent holes are evenly spaced at a bottom of the inner ring pipe and the outer ring pipe.

10. The method of claim 9, wherein an inner loop of vent holes and an outer loop of vent holes are evenly spaced at the bottom of the inner ring pipe and the outer ring pipe, said two loops of vent holes are equally spaced at either side of the perpendicular direction of the pipe center, each vent hole center and the perpendicular line of the pipe center respectively form an angle within the range of 15-40 degree with respect to the perpendicular direction of the pipe center.

11. The method of claim 9, wherein each vent hole is circular, and a combined diameter of the holes is 1 to 3 times as long as the cross section of the ring pipe.

12. A method for the selective hydrogenation of a cracked C8 fraction including styrene and phenylacetylene in a hydrogenation reactor loaded with a catalyst having an upper bed and a lower bed, the method comprising the steps of:
   feeding a feedstock comprising the cracked C8 fraction through a bottom of the lower bed at a first inlet temperature and contacting the feedstock with a first portion of the catalyst to produce a first hydrogenated product stream, wherein a temperature increase between the feedstock and the first hydrogenated product stream is controlled to be kept at 0-20° C. by introducing hydrogen from a first gas distributor positioned below the lower bed; and
   feeding the first hydrogenated product stream to the upper bed at a second inlet temperature and contacting the first hydrogenated product stream with a second portion of the catalyst to produce a second hydrogenated product stream, wherein a temperature increase between the first hydrogenated product stream and the second hydrogenated product stream is controlled to be kept at 0-15° C. by introducing hydrogen from a second gas distributer positioned below the upper bed; and sending the second hydrogenated product stream from the upper bed to a packing layer and recovering a hydrogenated product, wherein said hydrogenation reactor is operated at: a reactor inlet temperature in the range of 5-40° C., a reaction pressure in the range of 0.1-4.0 MPag, a hydrogen to feedstock ratio of the lower bed in the range of 0.1-50, a reaction oil phase space velocity within the range of 0.1-35 $h^{-1}$; and a weight ratio of the catalyst loaded in the upper bed and the lower bed is in the range of 1:1-0.5.

13. The method of claim 12, wherein the weight ratio of the catalyst loading in the upper bed to those in the lower bed is in the range of 1:0.8-0.6.

14. The method of claim 12, wherein said catalyst comprises $Al_2O_3$—$SiO_2$, $Al_2O_3$ or $SiO_2$ as a support and Ni as an active component, and additives comprising at least one metal from the group IVB, at least one metal from group VIB and at least one alkali metal; further wherein a total mass content of catalyst being 100%, Ni is present within the range of 12-21 wt %; the group IVB metal is present within the range of 0.6-8 wt %; the group VIB metal is present in the range of 0.5-1.5 wt %; the alkali metal is present within the range of 5-10 wt %; the group IVB metals are Ti and Zr; the group VIB metals are Cr, Mo and W; Alkali metals are Li, Na, and K.

15. The method of claim 12, wherein a BET specific surface area of the support is within the range of 140-200 $m^2$/g, pore volume is within the range of 0.2-0.5 ml/g, mean pore diameter is within the range of 10-25 nm, exhibiting parallel-peak structure.

16. A method for the selective hydrogenation of a cracked C8 faction including styrene and phenylacetylene in a hydrogenation reactor loaded with catalyst having an upper bed and a lower bed, the method comprising the steps of:

feeding a feedstock comprising the cracked C8 fraction through the bottom of the lower bed at a first inlet temperature and contacting the feedstock with a first portion of the catalyst to produce a first hydrogenated product stream, wherein a temperature increase between the feedstock and the first hydrogenated product stream is controlled to be kept at 0-20° C. by introducing hydrogen from a first gas distributor positioned below the lower bed; and feeding the first hydrogenated product stream to the upper bed at a second inlet temperature and contacting the first hydrogenated product stream with a second portion of the catalyst to produce a second hydrogenated product stream, wherein a temperature increase between the first hydrogenated product stream and the second hydrogenated product stream is controlled to be kept at 0-15° C. by introducing hydrogen from a second gas distributer positioned below the upper bed; and sending the second hydrogenated product stream from the upper bed to a packing layer and recovering a hydrogenated product, wherein said hydrogenation reactor is operated at: a reactor inlet temperature in the range of 5-40° C., a reaction pressure in the range of 0.1-4.0 MPag, a hydrogen to feedstock ratio of the lower bed in the range of 0.1-50, a reaction oil phase space velocity within the range of 0.1-35 $h^{-1}$; and the hydrogenation reactor has a circular cross section, the gas distributor comprises a horizontally installed inner ring pipe and an outer ring pipe, which are connected by connection pipes and linked to an air inlet vessel, wherein vent holes are evenly spaced at a bottom of the inner ring pipe and the outer ring pipe.

17. The method of claim 16, wherein an inner loop of vent holes and an outer loop of vent holes are evenly spaced at the bottom of the inner ring pipe and the outer ring pipe, said two loops of vent holes are equally spaced at either side of the perpendicular direction of the pipe center, each vent hole center and the perpendicular line of the pipe center respectively form an angle within the range of 15-40 degree with respect to the perpendicular direction of the pipe center.

18. The method of claim 16, wherein each vent hole is circular, and a combined diameter of the holes is 1 to 3 times as long as the cross section of the ring pipe.

19. The method of claim 16, wherein a weight ratio of the catalyst loaded in the upper bed and the lower bed is in the range of 1:1-0.5.

20. The method of claim 16, wherein a BET specific surface area of the support is within the range of 140-200 $m^2$/g, pore volume is within the range of 0.2-0.5 ml/g, mean pore diameter is within the range of 10-25 nm, exhibiting parallel-peak structure.

* * * * *